(12) United States Patent
Yang

(10) Patent No.: US 9,192,600 B2
(45) Date of Patent: Nov. 24, 2015

(54) COMBINATION THERAPY WITH NITRATED LIPIDS AND INHIBITORS OF THE RENIN-ANGIOTENSIN-ALDOSTERONE SYSTEM

(71) Applicant: The University of Utah Research Foundation, Salt Lake City, UT (US)

(72) Inventor: Tianxin Yang, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/183,468

(22) Filed: Feb. 18, 2014

(65) Prior Publication Data

US 2014/0243380 A1    Aug. 28, 2014

Related U.S. Application Data

(63) Continuation of application No. PCT/US2012/051304, filed on Aug. 17, 2012.

(60) Provisional application No. 61/525,543, filed on Aug. 19, 2011.

(51) Int. Cl.
| | |
|---|---|
| *A61K 31/41* | (2006.01) |
| *A61K 31/4178* | (2006.01) |
| *A61K 31/20* | (2006.01) |
| *A61K 31/201* | (2006.01) |
| *A61K 31/401* | (2006.01) |
| *A61K 45/06* | (2006.01) |

(52) U.S. Cl.
CPC ............. *A61K 31/4178* (2013.01); *A61K 31/20* (2013.01); *A61K 31/201* (2013.01); *A61K 31/401* (2013.01); *A61K 31/41* (2013.01); *A61K 45/06* (2013.01)

(58) Field of Classification Search
CPC ............ A61K 2300/00; A61K 31/201; A61K 31/4178; A61K 45/06
USPC ......................................................... 514/381
See application file for complete search history.

(56) References Cited

U.S. PATENT DOCUMENTS

2007/0232579 A1    10/2007    Freeman et al. ............... 514/178

FOREIGN PATENT DOCUMENTS

| WO | WO 01/15673 | 3/2001 | ............. A61K 31/00 |
|---|---|---|---|
| WO | WO 2005/110396 | 11/2005 | ............. A61K 31/21 |
| WO | WO 2009/017802 | 2/2009 | ............. A01N 37/00 |
| WO | WO 2009/129495 | 10/2009 | ............. G01N 31/00 |
| WO | WO 2009/149496 | 12/2009 | ................ A61P 9/10 |
| WO | WO 2009/155439 | 12/2009 | ........... A61K 31/201 |

OTHER PUBLICATIONS

International Preliminary Report on Patentability issued in corresponding foreign application, pp. 1-8 (Mar. 6, 2014).
European Search Report issued in corresponding foreign application, pp. 1-7 (Dec. 11, 2014).
Lui, Y., et al., "Combined Iosartan and nitro-oleic acid remarkably improves diabetic nephropathy in mice" *Am J Physiol Renal Physiol* 305: F1555-F1562 (2013).

*Primary Examiner* — My-Chau T Tran

(74) *Attorney, Agent, or Firm* — Pepper Hamilton LLP

(57) ABSTRACT

The present technology provides compositions and methods for treating chronic kidney disease, end-stage renal disease, or diabetic nephropathy. The compositions comprise a nitrated lipid and an inhibitor of the renin-angiotensin-aldosterone system. The methods comprise administering a nitrated lipid in combination with an inhibitor of the renin-angiotensin-aldosterone system to a subject in need thereof, in an amount effective to treat diabetic nephropathy, chronic kidney disease, and/or end-stage renal disease. The use of a nitrated lipid with an inhibitor of the renin-angiotensin-aldosterone system exhibits a synergistic effect in treating chronic kidney disease and diabetic nephropathy.

20 Claims, 5 Drawing Sheets

COMBINATION THERAPY WITH NITRATED LIPIDS AND INHIBITORS OF THE RENIN-ANGIOTENSIN-ALDOSTERONE SYSTEM

CROSS-REFERENCE TO RELATED PATENT APPLICATIONS

The present application is a continuation and claims priority under 35 U.S.C. §120 and §365(c) to PCT International Patent Application PCT/US2012/051304, filed Aug. 17, 2012, which claims priority to U.S. Provisional Application No. 61/525,543, filed Aug. 19, 2011, each of which are incorporated herein by reference in their entireties.

STATEMENT OF GOVERNMENT RIGHTS

This invention was made with government support under 079162 by the National Institutes of Health. The government has certain rights to this invention.

FIELD OF THE INVENTION

The present technology relates to compositions and methods for treating chronic kidney disease (CKD). More specifically, a combination of nitrated lipid and an inhibitor of the renin-angiotensin-aldosterone system may be used for treatment of CKD and end-stage renal disease, including, but not limited to, that associated with diabetes.

BACKGROUND OF THE INVENTION

Diabetes and diabetic complications represent a major public health problem, affecting 25 million Americans. In particular, diabetes and diabetic nephropathy constitute a major cause of CKD which progressively develops to end-stage renal disease (ESRD); patients with ESRD typically require dialysis or a kidney transplant. Currently, PPARγ agonists, thiazolidinediones (TZDs), are effective antidiabetic agents but are associated with severe edema, body weight gain and cardiovascular events. Inhibitors of the renin-angiotensin-aldosterone system (RAAS), which are widely used as anti-hypertensive agents, can help alleviate high blood pressure accompanying CKD but fail to stop the progression of CKD to ERSD. Indeed, in some instances, combination treatment with both an ACE inhibitor and an angiotensin receptor inhibitor has been shown to worsen major renal outcomes such as increasing serum creatinine and causing a greater decline in estimated glomerular filtration rate. Yusuf, S., et al., *New England J. Med.* (2008) 358 (15):1547-59.

SUMMARY

The present technology provides methods, compositions and medicaments useful in the treatment of chronic kidney disease and/or diabetic nephropathy. The methods involve administration of a nitrated lipid in combination with an inhibitor of RAAS to a subject in need thereof in amounts effective to treat the chronic kidney disease and/or diabetic nephropathy. This combination appears to be synergistic for reducing albuminuria, urinary and renal TBARS, and COX-2 mRNA expression in the kidney, all of which are diagnostic for diabetic nephropathy and chronic kidney disease (see FIGS. 1-4). Conversely, the combination of nitrated lipid and RAAS inhibitor synergistically increase the expression of renoprotective heme oxygenase 1 (HO-1) (FIG. 5). Hence, in one aspect there are provided compositions including a nitrated lipid and an inhibitor of RAAS for separate, simultaneous or sequential administration. Further, the use of a nitrated lipid and an inhibitor of RAAS in the preparation of a medicament for treatment of chronic kidney disease and/or diabetic nephropathy are provided.

The present methods include of treatment include administering an effective amount of a nitrated lipid and an inhibitor of the RAAS to a subject suffering from chronic kidney disease, diabetic nephropathy or hypertensive nephropathy. A variety of nitrated lipids may be used, including, but not limited to, nitro-fatty acids or esters thereof. Similarly, a variety of fatty acids are compatible with the disclosed methods, including, but not limited to, monounsaturated and polyunsaturated fatty acids. In some embodiments, the nitrated lipid is 9-nitrooleic acid, 10-nitrooleic acid or combinations thereof. In certain embodiments the RAAS inhibitor is an ACE inhibitor, a renin inhibitor or an angiotensin receptor inhibitor, e.g., losartan.

DETAILED DESCRIPTION

Figure 1:
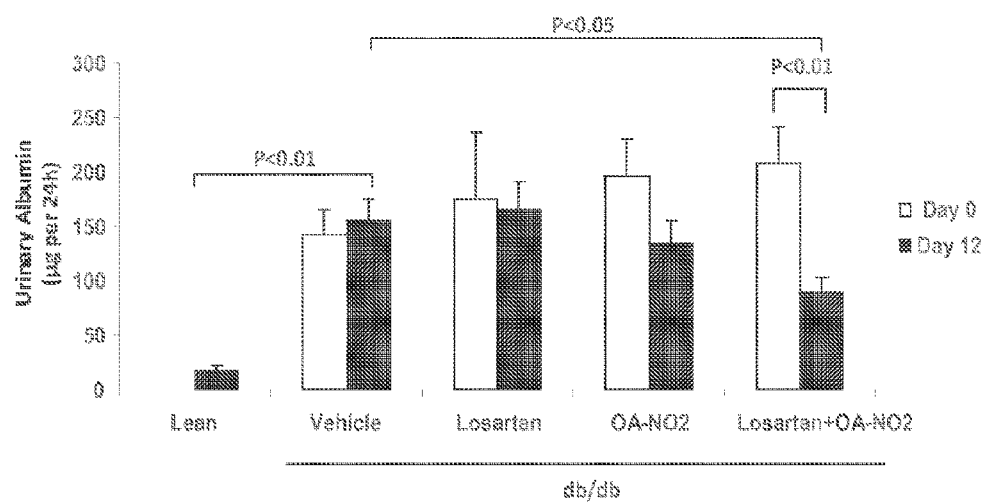
FIG. 1 is a bar graph comparing the amounts of urinary albumin in db/db mice before and after a 12 day (12-d) administration of vehicle, losartan, nitrooleic acid (OA-NO2), or losartan+OA-NO2. Lean mice (non-diabetic) with vehicle treatment were used as controls. losartan was administered via diet, while OA-NO2 and vehicle were each infused via osmotic mini-pump. Lean: n=5; vehicle: n=10; losartan: n=8; OA-NO2: n=9; losartan+OA-NO2: n=10. Data are mean±SE.

The following terms are used throughout as defined below.

"ACE inhibitor" is an inhibitor of the angiotensin I converting enzyme (ACE). ACE is a zinc proteinase that converts the peptide hormone angiotensin I to angiotensin II Inhibitors of ACE include Zn chelating functionality such as carboxyl or sulfhydryl groups.

Alkyl groups include straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups.

Alkenyl groups include straight and branched chain alkyl groups as defined above, except that at least one double bond exists between two carbon atoms. Thus, alkenyl groups have from 2 to 24 carbon atoms, and typically from 2 to 10 carbons or, in some embodiments, from 2 to 8, 2 to 6, or 2, 3 or 4 carbon atoms. Examples include, but are not limited to vinyl, allyl, $-CH=CH(CH_3)$, $-CH=C(CH_3)_2$, $-C(CH_3)=CH_2$, $-C(CH_3)=CH(CH_3)$, and $-C(CH_2CH_3)=CH_2$, among others.

"Diabetic nephropathy" refers to progressive kidney disease or damage due to diabetes. While the exact cause is not clear, it appears that high blood sugar leads to damage of the glomeruli and associated nephrons of the kidney. The resulting glomerulosclerosis, scarring and obstruction of the glomeruli, causes the kidney structures to begin to leak and protein begins to pass into the urine. The main sign of diabetic nephropathy is thus persistent protein in the urine (urinary albumin, also known as albuminuria).

Diabetic nephropathy is a leading cause of chronic kidney disease (CKD), where kidney function is lost over time until end-stage renal disease (ESRD) develops. ESRD is the complete or near-complete failure of the kidneys to function at a level needed for day-to-day life. ESRD usually occurs when diabetic nephropathy induced CKD worsens to the point where kidney function is less than 10% of normal. Subjects with ESRD typically require dialysis or a kidney transplant.

Oxidative stress is known to play an essential role in the pathogenesis of diabetic nephropathy. NADPH oxidase 4 (NOX4) is a major oxidant generating enzyme that is implicated to play a major pathogenic role in the development of diabetic nephropathy. A product from the oxidation of lipids by NOX4 or other oxidant generating systems is thiobarbituric acid reactive substances (TBARS). Thus, urinary and renal TBARS can be measured as an index of oxidative stress in diabetic nephropathy.

Cyclooxygnase-2 (COX-2) has been implicated to play a major role in the pathogenesis of diabetic nephropathy. In particular, increased renal COX-2 expression has been demonstrated in animal models of diabetic nephropathy and may serve as a marker of such a condition.

Heme oxygenase-1 (HO-1) is an enzyme that catalyzes the degradation of heme, resulting in the production of biliverdin, iron, and carbon monoxide. Abundant evidence supports a renoprotective role for HO-1 in various types of kidney injury. Raised levels of HO-1 may therefore indicate an enhanced renoprotective effect against chronic kidney disease and diabetic nephropathy.

The renin-angiotensin-aldosterone system (RAAS) is a hormonal system that is traditionally considered to play a major role in regulation of blood pressure and blood volume. Emerging evidence suggests that this system also plays a pro-inflammatory and pro-oxidative role in the pathogensis of CKD. In the RAAS, renin converts angiotensinogen (secreted by the liver) to angiotensin I. Angiotensin I is converted to angiotensin II by angiotensin converting enzyme (ACE). Angiotensin II binds to AT receptors to cause, among other effects, blood vessels to constrict and aldosterone to be released by the adrenal cortex, and also to elicit pro-inflammatory and pro-oxidant responses. Inhibitors of this system (e.g., ACE inhibitors, renin inhibitors and angtiotensin receptor inhibitors) are used therapeutically to lower blood pressure in hypertensive subjects and also to treat CKD.

"Renin inhibitor" is an inhibitor of the aspartic proteinase, renin. The latter enzyme, as part of the RAAS, converts the peptide angiotensinogen to angiotensin I.

"Treating" means an alleviation, in whole or in part, of symptoms associated with a condition or disorder (e.g., disease), or halt of further progression or worsening of those symptoms. Similarly, as used herein, an "effective amount" of a compound disclosed herein refers to an amount of the compound that alleviates, in whole or in part, symptoms associated with a condition or disorder, or halts further progression or worsening of those symptoms. For example, in treating diabetic nephropathy or chronic kidney disease, a slowed or halted increase in albuminuria or a decrease in albuminuria are examples of desirable treatment results. In another example, treating diabetic or chronic kidney disease may include slowing or halting the increase in urinary or renal TBARS or a decrease in COX-2 expression. Further, treating does not necessarily occur by administration of one dose of the compound, but often occurs upon administration of a series of doses. Thus, an effective amount may be administered in one or more doses.

The compositions and methods disclosed herein make use of nitrated lipids. Nitrated lipids are lipids comprising at least one nitro ($NO_2$) group covalently bonded to the lipid. The methods disclosed herein encompass administration of a single type of nitrated lipid or a mixture of two or more different types of nitrated lipids. By way of example, 9-nitro-9-cis-octadecenoic acid is one type of nitrated lipid. A single type of nitrated lipids is distinguished from other types by the identity of the lipid and number and position of $NO_2$ groups.

A variety of lipids may be used to form the nitrated lipids. In general, useful lipids include, but are not limited to, fats and fat-derived materials. In some embodiments, the lipid is a fatty alcohol, sterol, or complex lipid. Examples of complex lipids include, but are not limited to, glycerolipids (e.g., compounds having a glycerol backbone including, but not limited to, phospholipids, glycolipids, monoglycerides, diglycerides, triglycerides) or cholesterol (e.g., cholesterols having fatty acids attached to it such as cholesterol linoleate). Other examples of nitrated lipids include, but are not limited to, those disclosed in U.S. Patent Publication No. 2007/0232579.

Alternatively, the lipid is a fatty acid or ester thereof such as a $C_8$-$C_{24}$ fatty acid or ester. In some embodiments the fatty acid or ester is a $C_{10}$-$C_{22}$, $C_{12}$-$C_{20}$, $C_{14}$-$C_{18}$ or $C_{14}$-$C_{22}$ fatty acid or ester. A fatty acid is alkyl or alkenyl in which the terminal carbon is a COOH group. In some embodiments, the alkyl or alkenyl is a $C_8$-$C_{24}$ alkyl or alkenyl. In other embodiments, the alkyl or alkenyl has 9, 10, 11, 12, 13, 14, 15, 16, 17, 18, 19, 20, 21, 22, or 23 carbons or falls in a range between and including any two values thereof. In some embodiments, the alkyl or alkenyl is branched or unbranched. A wide variety of fatty acids may be used, including, but not limited to monounsaturated fatty acids and polyunsaturated fatty acids. In some embodiments, the monounsaturated fatty acid is oleic acid or linoleic acid. In some embodiments, the oleic acid is 9-nitrooleic acid, 10-nitrooleic acid, or combinations thereof.

Nitrated lipids may be synthesized according to known procedures. For example, U.S. Patent Publication No. 2007/

0232579 discloses a procedure comprising the steps of reacting a lipid with a mercuric salt, a selenium compound, and a nitrating compound to produce a first intermediate and reacting the first intermediate with an oxidant. Useful mercuric salts, selenium compounds, nitrating compounds, oxidants, relative amounts of reactants, and reaction conditions are also disclosed in U.S. Patent Publication No. 2007/0232579. Such synthetic procedures may provide mixtures of two or more types of nitrated lipids which may be separated or purified by techniques known in the art, if desired.

The lipids described above may be obtained from a variety of sources. For example, lipids may be commercially available or may be obtained from natural sources. Plant oils, including, but not limited to olive oil, linseed oil, flaxseed oil, rapeseed oil, and perilla oil are possible natural sources of fatty acid lipids. Fish oils or other marine oils are other possible sources of fatty acids. Nitrated lipids present in any of these or other natural sources may be extracted and/or purified for use in the methods disclosed herein.

In one aspect, the present technology provides compositions including a nitrated lipid and an inhibitor of the renin-angiotensin-aldosterone system. In some embodiments of the present compositions, the nitrated lipid is a nitrated monounsaturated fatty acid or a nitrated polyunsaturated fatty acid. In some embodiments, the nitrated lipid is a nitrooleic acid or a nitrolinoleic acid such as, e.g., 9-nitrooleic acid, 10-nitrooleic acid, or a combination thereof.

The inhibitor of the RAAS may be any such inhibitor known in the art such as an ACE inhibitor, a renin inhibitor, or an angiotensin receptor antagonist. In some embodiments, the inhibitor of the RAAS is an ACE inhibitor such as enalapril, ramipril, quinapril, perindopril, lisinopril, benazepril, imidapril, zofenopril, fosinopril, or captopril. In certain embodiments, the inhibitor of the RAAS is an angiotensin receptor inhibitor such as losartan, valsartan, telmisartan, irbesartan, azilsartan, olmesartan, candesartan, or eprosartan. For example, in some embodiments, the inhibitor of the RAAS is losartan. In certain embodiments, the inhibitor of the RAAS is a renin inhibitor such as aliskiren, remikiren, or renin siRNA. In some embodiments, the present compositions may include two or more inhibitors of the renin-angiotensin-adosterone system. For example, compositions of the present technology may include an ACE inhibitor and losartan.

In some embodiments, the composition of the present technology is a pharmaceutical composition that includes any of the compositions disclosed herein and a pharmaceutically acceptable additive, such as, e.g., pharmaceutically acceptable carriers and excipients. The pharmaceutical composition may be any number of pharmaceutical formulations capable of various administration routes e.g., oral administration, topical administration, transdermal administration, by nasal administration, rectal administration, subcutaneous injection, intravenous injection, intramuscular injection, or intraperitoneal injection. The formulations can take the form of granules, powders, tablets, capsules, syrup, suppositories, injections, emulsions, elixirs, suspensions or solutions. These formulations may further include a variety of well-known pharmaceutically acceptable additives, carriers, and/or excipients as necessary. Any of the formulations, delivery methods, and pharmaceutically acceptable additives, carriers, and excipients disclosed in U.S. Patent Publication No. 2007/0232579 may also be used in the pharmaceutical composition described herein.

Combinations of the present technology may be administered separately, simultaneously, or sequentially. Thus, the present technology provides for the administering of each of the components separately but as part of the same therapeutic treatment program or regimen, and it is contemplated that separate administration of each compound, at different times and by different routes, will sometimes be recommended. Thus the two components need not necessarily be administered at essentially the same time. In the one embodiment the nitrated lipid will be given one or more days prior to or after the administration of the inhibitor of the RAAS either daily or "on demand". In another embodiment, administration is timed so that the peak pharmacokinetic effect of the nitrated lipid precedes or coincides with the peak pharmacokinetic effect of RAAS inhibitor. In some embodiments, both components are administered in an oral dosage form.

In some embodiments, the present technology provides a kit that includes a separate or combined composition(s) that include the nitrated lipid and the inhibitor of the renin-antiotensin-aldosterone system. The kit may include a container for containing the separate compositions such as a divided bottle or a divided foil packet, wherein each compartment contains a plurality of dosage forms (e.g., tablets) comprising either the nitrated lipid or the RAAS inhibitor. Alternatively, rather than separating the active ingredient-containing dosage forms, the kit may contain separate compartments each of which contains a whole dosage which comprises separate compositions. An example of this type of kit is a blister pack wherein each individual blister contains two tablets, one tablet comprising the nitrated lipid, the other comprising the RAAS inhibitor. The nitrated lipid and the inhibitor of the renin-antiotensin-aldosterone system may also be formulated as a single composition for simultaneous administration, e.g., a single tablet or capsule.

Typically the kit comprises directions for the administration of the separate components. Such instructions would cover situations such as:

i) the dosage form in which the components are administered (e.g. oral and parenteral), ii) when the component parts of the product are administered at different dosage intervals, or iii) when titration of the individual components of the combination is desired by the prescribing physician. The container may have deposited thereon a label that describes the contents therein and any appropriate warnings.

In another aspect the present technology provides method of treatment for chronic kidney disease, diabetic nephropathy and/or hypertensive nephropathy. In some embodiments of the methods, the subject has chronic kidney disease or end-stage renal disease. The methods include administering a nitrated lipid in combination with an inhibitor of the RAAS to a subject in need thereof, in an amount effective to treat chronic kidney disease, end-stage renal disease, diabetic nephropathy and/or hypertensive nephropathy. In some embodiments of the methods, the nitrated lipid is a nitrated monounsaturated fatty acid or a polyunsaturated fatty acid. In some embodiments, the nitrated lipid is a nitrooleic acid or a nitrolinoleic acid. For example, the nitrated lipid may be selected from 9-nitrooleic acid, 10-nitrooleic acid, or combinations thereof.

In methods of the present technology, the inhibitor of the RAAS can be an ACE inhibitor, a renin inhibitor, or a angiotensin receptor antagonist. Thus, the inhibitor of the RAAS may be, e.g., enalapril, ramipril, quinapril, perindopril, lisinopril, benazepril, imidapril, zofenopril, fosinopril, or captopril. In some embodiments, the inhibitor of the RAAS can be losartan, valsartan, telmisartan, irbesartan, azilsartan, olmesartan, candesartan, or eprosartan. In some embodiments, the inhibitor of the RAAS is losartan. In certain embodiments, the inhibitor of the RAAS can be aliskiren, remikiren, or renin siRNA. In the present methods, two or more inhibitor of the RAAS may be employed. In some embodiments of the methods, the inhibitor of the RAAS is an ACE inhibitor and losartan.

In another aspect of the present technology, the combinations and compositions disclosed herein may be used in a prophylactic manner to prevent diabetic nephropathy or hypertensive nephropathy. In particular, there are provided methods including administering a nitrated lipid in combination with an inhibitor of the RAAS to a subject in need thereof, in an amount effective to prevent chronic kidney disease or end-stage renal disease. Any of the nitrated lipids, the inhibitors of the renin-angitotensin-aldosterone system, or compositions comprising such compounds as disclosed herein may be used in such methods. For example, in some embodiments, the nitrated lipid is selected from 9-nitrooleic acid, 10-nitrooleic acid, or combinations thereof. In some embodiments, the inhibitor of the RAAS is losartan.

Specific effective amounts of the nitrated lipids to be administered will vary depending upon a variety of factors, e.g., the condition to be treated, the age, body weight, general health, sex, and diet of the subject, the dose intervals, and the administration route.

In some embodiments, the effective amount of the nitrated lipid ranges from about 1 µg per day to about 100 mg per day, from about 1 mg per day to about 50 mg per day, from about 1 mg per day to about 25 mg per day, or from about 2 mg per day to about 10 mg per day.

Any of the nitrated lipids disclosed herein may be administered to the subject alone or in combination with one or more other therapeutic agents. By "administered in combination," it is meant that the nitrated lipids and the therapeutic agents may be administered as a single composition, simultaneously as separate doses, or sequentially. Sequential administration refers to administering the nitrated lipids and at least one therapeutic agent either before or after one another.

The nitrated lipids may be administered to a subject via any number of pharmaceutical formulations and administration routes. The formulations can take the form of granules, powders, tablets, capsules, syrup, suppositories, injections, emulsions, elixirs, suspensions or solutions. These formulations may further include a variety of well-known pharmaceutically acceptable additives, carriers, and/or excipients as necessary. The formulations may be delivered to the subject by various routes of administration, e.g., by topical administration, transdermal administration, oral administration, by nasal administration, rectal administration, subcutaneous injection, intravenous injection, intramuscular injection, or intraperitoneal injection. Any of the formulations, delivery methods, and pharmaceutically acceptable additives, carriers, and excipients disclosed in U.S. Patent Publication No. 2007/0232579 may also be used with the methods described herein. Another possible route of administration includes incorporating the nitrated lipid into various food products. Food products, include, but are not limited to butter, margarine, vegetable oils, and the like.

The subjects of the disclosed methods include any animal that can benefit from the administration of a nitrated lipid. In some embodiments, the subject is a mammal, e.g., a human, a primate, a dog, a cat, a horse, a cow, a pig, or a rodent, e.g., a rat or mouse. Typically, the mammal is a human.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

For the purposes of this disclosure and unless otherwise specified, "a" or "an" means "one or more."

The present invention, thus generally described, will be understood more readily by reference to the following examples, which are provided by way of illustration and are not intended to be limiting of the present invention.

EXAMPLES

Materials and Methods

Animals. Male 3-4-month-old db/db mice were from Jackson Laboratories (Bar Harbor, Me.). All animals were housed in an air-conditioned room with a 12-hour light/dark cycle. All procedures and protocols were in accordance with guidelines set by the Laboratory Animal Care Committee at the University of Utah.

Materials. 9-Nitrooleic acid and 10-nitrooleic acid are two regioisomers of nitrooleic acid (OA-NO$_2$), which are formed by nitration of oleic acid in approximately equal proportions (Hayama et al. Chemistry Letters pp. 1109-1112, 1982). The two compounds were purchased from Cayman Chemicals (Ann Arbor, Mich.) (9-nitrooleic acid: Cat#10008042; 10-nitrooleic acid: Cat#10008043) and used as an 1:1 mixture of the isomers.

Protocols for Animal Experiments db/db mice were implanted with a 3-week osmotic minipump which delivered a vehicle or OA-NO$_2$ at 10 mg/kg/d. Animals were fed with losartan, which is an AT1 blocker. 24-h urine samples were collected before and after the treatment.

Example 1

Measurement of Urinary Albumin in Diabetic Mice Treated with Nitrated Oleic Acid, Losartan or Both As compared with lean mice, untreated db/db mice developed severe albuminuria (FIG. 1) over the course of the 12-day study. Neither losartan or OA-NO2 alone exhibited a statistically significant effect on urinary albumin excretion. In contrast, the combination of the two drugs induced a synergistic reduction of urinary albumin excretion (P<0.05). The changes of urinary albumin relative to the vehicle group by Losartan alone, OA-NO2 alone, and Losartan+OANO2 were +7%, −13%, and −42.6%. The plus symbol (+) means an increase and the minus symbol (−) indicates a decrease in albuminuria.

Example 2

Figure 2:
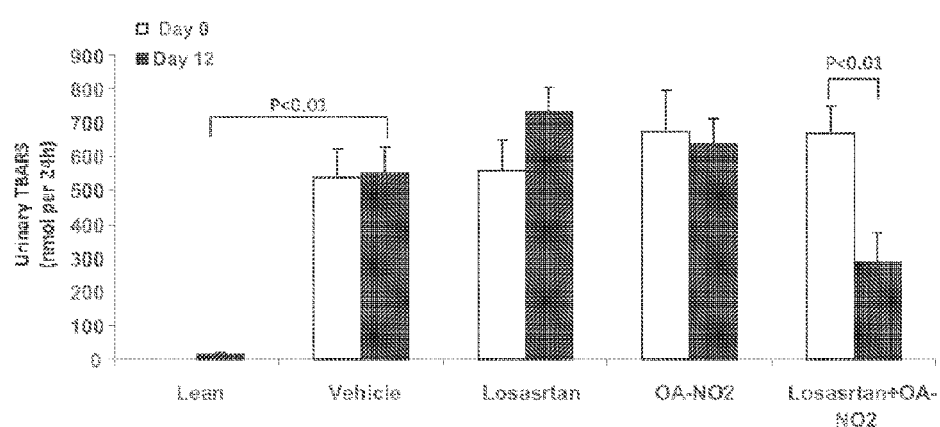
FIG. 2 is a bar graph comparing the amounts of urinary thiobarbituric acid reactive substances (TBARS) in db/db mice before and after 12-d infusion with vehicle, losartan, nitrooleic acid (OA-NO2), or losartan+OA-NO2. Lean mice (non-diabetic) with vehicle treatment were used as controls. Losartan was administered via diet, while vehicle and OA-NO2 were each infused via osmotic mini-pump. Lean: n=5; vehicle: n=10; losartan: n=8; OA-NO2: n=9; losartan+OA-NO2: n=10. Data are mean±SE.
Figure 3:
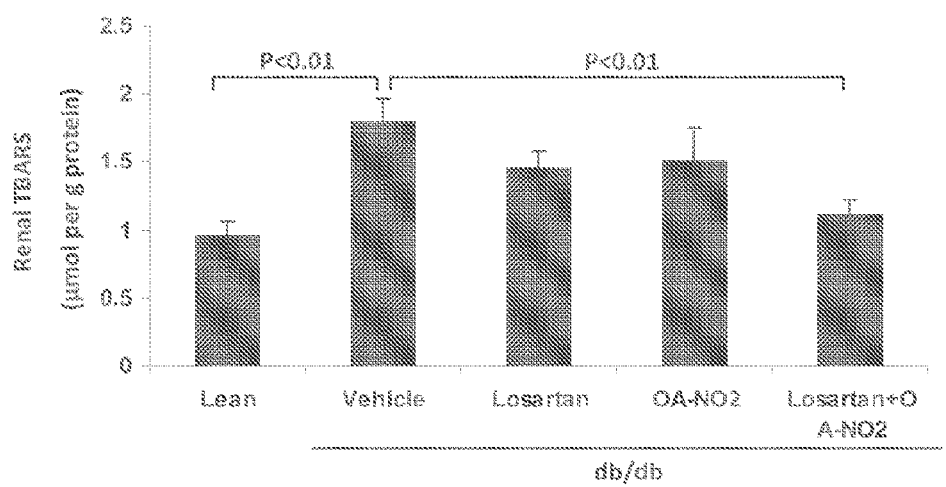
FIG. 3 is a bar graph showing the amounts of renal TBARS in db/db mice after a 12-d administration of vehicle, losartan, nitrooleic acid (OA-NO2), or losartan+OA-NO2. Lean mice (non-diabetic) with vehicle treatment were used as controls. Losartan was administered via diet, while vehicle and OA-NO2 were infused via osmotic mini-pump. Lean: n=5; vehicle: n=10; losartan: n=8; OA-NO2: n=9; losartan+OA-NO2: n=10. Data are mean±SE.

Measurement of Urinary and Renal TBARS in Diabetic Mice Treated with Nitrated Oleic Acid, Losartan or Both Untreated diabetic mice exhibited significant urinary and renal TBARS (FIGS. 2-3). The combination of OA-NO$_2$ and losartan induced a striking reduction of urinary TBARS whereas treatment with only one of OA-NO$_2$ or losartan was without an effect (FIG. 2). The changes of urinary TBARS relative to the vehicle group after 12 days for losartan alone, OA-NO2 alone, and losartan+OANO2 were +33.4%, +16.5%, and −47.6%, %, respectively. Renal TBARS content in each of losartan alone and OA-OA2 alone group showed a trend of reduction but none of these changes reached statistical significance. A statistically significant reduction was only found in the losartan+OA-NO2 group (FIG. 3).

Example 3

Figure 4:
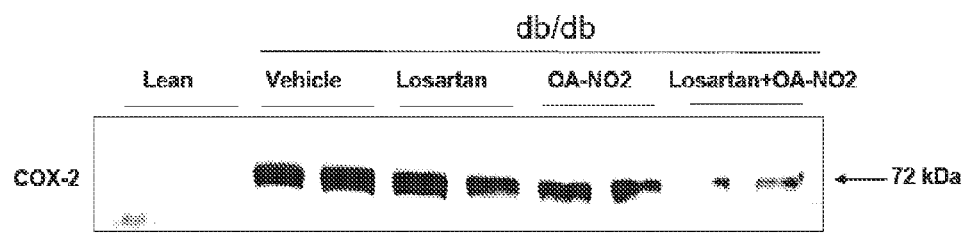
FIG. 4 shows the amounts of renal COX-2 protein in db/db mice after a 12-d administration of vehicle, losartan, nitrooleic acid (OA-NO2), or losartan+OA-NO2. Lean mice (non-diabetic) with vehicle treatment were used as controls. Renal COX-2 protein was analyzed by using immunoblotting. Shown are representative results from 2 animals per group.

Measurement Renal COX-2 Protein Expression in Diabetic Mice Treated with Nitrated Oleic Acid, Losartan, or Both Renal COX-2 expression in db/db mice treated as above was examined by immunoblotting. As compared with lean controls, a marked induction of COX-2 protein expression was found in the db/db vehicle group. Losartan or OA-NO2 alone only produced a modest effect on renal COX-2 expression (FIG. 4). In contrast, the COX-2 expression was significantly suppressed in the losartan+OA-NO2 group (FIG. 4). The changes of renal COX-2 protein expression relative to the vehicle group by losartan alone, OA-NO2 alone, and losartan+OANO2 were −5.3%, −14.8%, and −38.8%, respectively.

Example 4

Figure 5:
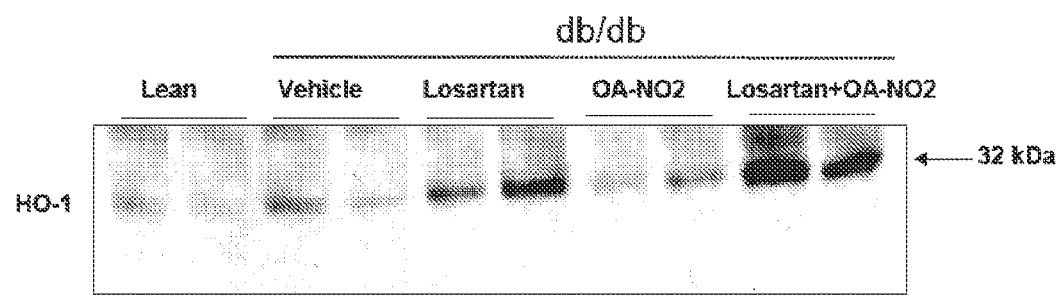
FIG. 5 shows the amounts of renal heme oxygenase-1(HO-1) protein in db/db mice after a 12-d administration of vehicle, losartan, nitrooleic acid (OA-NO2), or losartan+OA-NO2. Lean mice (non-diabetic) with vehicle treatment were used as controls. Renal HO-1 protein was analyzed by using immunoblotting. Shown are representative results from 2 animals per group.

Measurement Renal Heme Oxygenase-1 Protein Expression in Diabetic Mice Treated with Nitro-Oleic Acid, Losartan, or Both Renal HO-1 expression was examined using immunoblotting. Either losartan or OA-NO2 alone elevated renal HO-1 expression and the combination of the two agents produced a much greater (synergistic) effect (FIG. 5). The changes of renal HO-1 protein expression relative to the vehicle group by losartan alone, OA-NO2 alone, and losartan+OA-NO2 were +97.6%, +48.8%, and +211.4%, respectively.

Overall, consistent results from analysis of the above-mentioned 5 key parameters relevant to the diabetic kidney injury demonstrated that renoprotective action of the combination of Losarton and OA-NO2 is greater than the additive effects of the single treatments. These results provide compelling evidence supporting a strong synergy between nitrated fatty acids and an inhibitor of renin-angiotensin system in management of diabetic nephropathy.

What is claimed is:

1. A composition comprising a nitrated lipid or a metabolite thereof, and an inhibitor of the renin-angiotensin-aldosterone system.

2. The composition of claim 1, wherein the nitrated lipid comprises a monounsaturated fatty acid or a polyunsaturated fatty acid.

3. The composition of claim 1, wherein the nitrated lipid is a nitrooleic acid or a nitrolinoleic acid.

4. The composition of claim 1, wherein the nitrated lipid is selected from 9-nitrooleic acid, 10-nitrooleic acid, or combinations thereof.

5. The composition of claim 1, wherein the inhibitor of the renin-angiotensin-aldosterone system is an ACE inhibitor, a renin inhibitor, or an angiotensin receptor antagonist.

6. The composition of claim 1, comprising an additional inhibitor of the renin-angiotensin-aldosterone system.

7. The composition of claim 6, comprising an ACE inhibitor and losartan.

8. A pharmaceutical composition comprising a nitrated lipid or a metabolite thereof, an inhibitor of the renin-angiotensin-aldosterone system, and a pharmaceutically acceptable carrier, excipient, adjuvant, or a combination thereof.

9. A kit comprising a separate or combined composition comprising the nitrated lipid or the inhibitor of the renin-angiotensin-aldosterone system.

10. A method comprising administering a nitrated lipid or a metabolite thereof and an inhibitor of the renin-angiotensin-aldosterone system to a subject in need thereof, in an amount effective to treat chronic kidney disease or diabetic nephropathy.

11. The method of claim 10, wherein the nitrated lipid is a nitrated monounsaturated fatty acid or a nitrated polyunsaturated fatty acid.

12. The method of claim 10 wherein the nitrated lipid is a nitrooleic acid or a nitrolinoleic acid.

13. The method of claim 10, wherein the nitrated lipid is selected from 9-nitrooleic acid, 10-nitrooleic acid, or combinations thereof.

14. The method of claim 10, wherein the inhibitor of the renin-angiotensin-aldosterone system is an ACE inhibitor, a renin inhibitor, or an angiotensin receptor antagonist.

15. The method of claim 10, comprising two or more inhibitors of the renin-angiotensin-aldosterone system.

16. The method of claim 10, wherein administration of the nitrated-lipid and the inhibitor of the renin-angiotensin-aldosterone system is contemporaneous.

17. The method of claim 10, wherein administration of the nitrated-lipid and the inhibitor of the renin-angiotensin-aldosterone system is sequential.

18. The method of claim 10, wherein the subject has chronic kidney disease or end-stage renal disease.

19. The method of claim 18, wherein the nitrated lipid is a monounsaturated fatty acid selected from 9-nitrooleic acid, 10-nitrooleic acid, or combinations thereof.

20. The method of claim 18, wherein the inhibitor of the renin-angiotensin-aldosterone system is losartan.

* * * * *